US012642541B2

(12) United States Patent
Grostefon et al.

(10) Patent No.: US 12,642,541 B2
(45) Date of Patent: Jun. 2, 2026

(54) COMBINATION DRILL GUIDE AND DEPTH GAUGE SURGICAL INSTRUMENT FOR IMPLANTING AN ACETABULAR CUP COMPONENT AND ASSOCIATED SURGICAL METHOD

(71) Applicant: DePuy Synthes Products, Inc., Raynham, MA (US)

(72) Inventors: Justin D. Grostefon, Warsaw, IN (US); James K. Naylor, Greater Manchester (GB); Brett M. DeBenedictis, East Bridgewater, MA (US); Karthikeyan Arumugam, Zuchwil (CH); Kariyamapudi Gopinath, Chennai (IN); Kathiresan Ramu, Zuchwil (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 18/830,461

(22) Filed: Sep. 10, 2024

(65) Prior Publication Data

US 2024/0423650 A1      Dec. 26, 2024

Related U.S. Application Data

(63) Continuation of application No. 17/500,163, filed on Oct. 13, 2021, now Pat. No. 12,082,828.

(51) Int. Cl.
| | |
|---|---|
| *A61B 17/17* | (2006.01) |
| *A61B 17/16* | (2006.01) |
| *A61B 90/00* | (2016.01) |
| *A61B 17/56* | (2006.01) |

(52) U.S. Cl.
CPC ...... *A61B 17/1746* (2013.01); *A61B 17/1613* (2013.01); *A61B 17/1666* (2013.01); *A61B*

*90/06* (2016.02); *A61B 2017/564* (2013.01); *A61B 2090/062* (2016.02)

(58) Field of Classification Search
CPC .............. A61L 7/1746; A61B 17/1666; A61B 17/1626; A61B 17/7092; A61B 2090/062
See application file for complete search history.

(56) References Cited

U.S. PATENT DOCUMENTS

| | | | | |
|---|---|---|---|---|
| 5,928,243 | A | * | 7/1999 | Guyer ................ A61B 17/1671 |
| | | | | 606/102 |
| 7,131,974 | B2 | | 11/2006 | Keyer et al. |
| 9,788,880 | B2 | * | 10/2017 | Barsoum ................ A61B 17/16 |
| 10,172,630 | B2 | | 1/2019 | Ponzer et al. |

(Continued)

FOREIGN PATENT DOCUMENTS

EP          3494906 A1      6/2019

OTHER PUBLICATIONS

International Search Report, Application No. PCT/IB2022/058630, dated Dec. 13, 2022, 6 pages.

*Primary Examiner* — Matthew J Lawson
(74) *Attorney, Agent, or Firm* — Barnes & Thornburg LLP

(57)          ABSTRACT

A combination drill guide and depth gauge surgical instrument and associated method for use during a surgical procedure to implant an acetabular cup component into a surgically-prepared acetabulum of a patient's hip includes an elongated shaft having a drill guide on an end thereof. The instrument also includes a retractable depth probe that may be used to gauge the depth of the holes drilled by use of the drill guide.

18 Claims, 11 Drawing Sheets

(56)                    References Cited

U.S. PATENT DOCUMENTS

| | | | |
|---|---|---|---|
| 2003/0233098 A1* | 12/2003 | Markworth | A61B 17/17 |
| | | | 606/96 |
| 2009/0012526 A1* | 1/2009 | Fletcher | A61B 17/1615 |
| | | | 606/87 |
| 2010/0106151 A1 | 4/2010 | Longo et al. | |
| 2016/0128704 A1 | 5/2016 | McGinley et al. | |
| 2019/0167446 A1* | 6/2019 | Conrad | A61B 17/1742 |
| 2019/0231588 A1 | 8/2019 | Mikkonen et al. | |
| 2019/0269469 A1 | 9/2019 | Bush, Jr. et al. | |
| 2020/0000464 A1* | 1/2020 | Gaston | A61B 17/10 |
| 2020/0289172 A1* | 9/2020 | Hoos | A61B 90/36 |
| 2022/0104902 A1* | 4/2022 | Conley | G01B 3/28 |

* cited by examiner

COMBINATION DRILL GUIDE AND DEPTH GAUGE SURGICAL INSTRUMENT FOR IMPLANTING AN ACETABULAR CUP COMPONENT AND ASSOCIATED SURGICAL METHOD

This application is a continuation application and claims priority to U.S. patent application Ser. No. 17/500,163, now U.S. Pat. No. 12,082,828, which was filed on Oct. 13, 2021, the entirety of which is hereby incorporated by reference.

TECHNICAL FIELD

The present disclosure relates generally to orthopaedic surgical instruments and, more particularly, to surgical instruments used to install an acetabular cup component.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular cup component and a femoral head component. An acetabular cup component generally includes an outer shell configured to engage the acetabulum of the patient and an inner bearing or liner coupled to the shell and configured to engage the femoral head. The femoral head component and inner liner of the acetabular component form a ball and socket joint that approximates the natural hip joint.

To facilitate the replacement of the natural joint with a prosthetic hip joint, orthopaedic surgeons may use a variety of orthopaedic surgical instruments such as, for example, drill guides, drills, depth gauges and/or other surgical instruments.

SUMMARY

According to one aspect, a combination drill guide and depth gauge surgical instrument for use during a surgical procedure to implant an acetabular cup component into a surgically-prepared acetabulum of a patient's hip includes an elongated body having a drill guide secured to an end thereof. The drill guide has a guide bore extending therethrough. The elongated body also includes an elongated channel extending parallel to a longitudinal axis of the elongated body. The instrument also includes a depth probe positioned in the elongated channel. The depth probe has a distal tip extending out of an open end of the elongated channel. The instrument also includes a thumb actuator movable relative to the elongated body and operable to move the depth probe such that the depth probe's distal tip is extended and retracted relative to the open end of the elongated channel.

In an embodiment, the thumb actuator includes a slider button secured to the depth probe and operable to slide along an upper surface of the elongated body. Movement of the slider button in a direction toward the open end of the elongated channel causes the depth probe's distal tip to be extended away from the open end of the elongated channel. Oppositely, movement of the slider button in a direction away the open end of the elongated channel causes the depth probe's distal tip to be retracted back toward the open end of the elongated channel.

The upper surface of the elongated body may have a plurality of depth marks disposed thereon, with each of the plurality depth marks being positioned at a location on the upper surface of the elongated body corresponding to a depth of the depth probe's distal tip. In such an arrangement, the slider button has a depth indicator disposed thereon, with the depth indicator being alignable with one of the plurality of depth marks based on the position of the slider button.

In another embodiment, the thumb actuator may include a knob operatively coupled to the depth probe, with the knob being rotatable relative to the elongated body. In such an arrangement, rotational movement of the knob in a direction toward the open end of the elongated channel causes the depth probe's distal tip to be extended away from the open end of the elongated channel. Oppositely, rotational movement of the knob in a direction away from the open end of the elongated channel causes the depth probe's distal tip to be retracted back toward the open end of the elongated channel.

In an embodiment, the depth probe has a plurality of depth marks disposed thereon, with each of the plurality depth marks being positioned at a location on the depth probe corresponding to a depth of the depth probe's distal tip. In such an arrangement, the upper surface of the elongated body has a viewing window formed therein, with one of the plurality of depth marks being viewable through the viewing window based on an amount and direction of rotational movement of the knob.

In an exemplary embodiment, the open end of the elongated channel is positioned proximate to the drill guide. In such an arrangement, movement of the thumb actuator in a direction toward the open end of the elongated channel causes the depth probe's distal tip to be advanced into and through the guide bore of the drill guide.

In such an exemplary embodiment, movement of the thumb actuator in a direction away from the open end of the elongated channel causes the depth probe's distal tip to be advanced out of the guide bore of the drill guide.

In an embodiment, the elongated body is formed from a polymeric material, and the depth probe is formed from a flexible polymeric material.

In another embodiment, the elongated body is formed from a polymeric material, and a metallic drill bushing is positioned in the guide bore of the drill guide.

In an illustrative embodiment, the open end of the elongated channel is positioned on an end of the elongated body opposite the drill guide, and movement of the thumb actuator in a direction toward the open end of the elongated channel causes the depth probe's distal tip to be advanced in a direction opposite the drill guide.

According to another aspect, a combination drill guide and depth gauge surgical instrument for use during a surgical procedure to implant an acetabular cup component into a surgically-prepared acetabulum of a patient's hip includes an elongated body having a drill guide secured to an end thereof. The drill guide has a guide bore extending therethrough. The elongated body also includes an elongated channel extending parallel to a longitudinal axis of the elongated body. A depth probe is positioned in the elongated channel, with the depth probe having a distal tip extending out of an open end of the elongated channel. The open end of the elongated channel is positioned proximate to the drill guide. A thumb actuator is movable relative to the elongated body and operable to move the depth probe such that the depth probe's distal tip is extended into and through the guide bore of the drill guide.

The thumb actuator may include a slider button secured to the depth probe, with the slider button being operable to slide along an upper surface of the elongated body. In such an arrangement, movement of the slider button in a direction toward the guide bore of the drill guide causes the depth probe's distal tip to be extended into and through the guide bore of the drill guide. Oppositely, movement of the slider button in a direction away the guide bore of the drill guide causes the depth probe's distal tip to be retracted back through and out of the guide bore of the drill guide.

In such an embodiment, the upper surface of the elongated body has a plurality of depth marks disposed thereon, with each of the plurality depth marks being positioned at a location on the upper surface of the elongated body corresponding to a depth of the depth probe's distal tip. The slider button may have a depth indicator disposed thereon, with the depth indicator being alignable with one of the plurality of depth marks based on the position of the slider button.

In another embodiment, the thumb actuator may include a knob operatively coupled to the depth probe and rotatable relative to the elongated body. In such an arrangement, rotational movement of the knob in a direction toward the guide bore of the drill guide causes the depth probe's distal tip to be extended into and through the guide bore of the drill guide. Oppositely, rotational movement of the knob in a direction away from the guide bore of the drill guide causes the depth probe's distal tip to be retracted back through and out of the guide bore of the drill guide.

In such an embodiment, the depth probe may have a plurality of depth marks disposed thereon, with each of the plurality depth marks being positioned at a location on the depth probe corresponding to a depth of the depth probe's distal tip. In such an arrangement, the upper surface of the elongated body may have a viewing window formed therein, with one of the plurality of depth marks being viewable through the viewing window based on an amount and direction of rotational movement of the knob.

In an embodiment, the elongated body is formed from a polymeric material, and the depth probe is formed from a flexible polymeric material.

In another embodiment, the elongated body is formed from a polymeric material, and a metallic drill bushing is positioned in the guide bore of the drill guide.

According to another aspect, a method of implanting an acetabular cup component into a surgically-prepared acetabulum of a patient's hip includes positioning a drill guide of a combination drill guide and depth gauge surgical instrument in a desired position within the surgically-prepared acetabulum of the patient's hip and thereafter advancing a bone drill through drill guide and drilling a hole into bone tissue of the patient's hip. Thereafter, the bone drill is removed from the drill guide, and a depth probe of the combination drill guide and depth gauge surgical instrument is advanced through the drill guide so that a depth of the drilled hole may be determined.

A bone screw is installed in the drilled hole after the depth of the drilled hole has been determined.

The combination drill guide and depth gauge surgical instrument may be embodied as a single-use instrument. In such a case, the combination drill guide and depth gauge surgical instrument is disposed of subsequent to installation of the bone screw.

BRIEF DESCRIPTION OF THE DRAWINGS

The detailed description particularly refers to the following figures, in which.

DETAILED DESCRIPTION OF THE DRAWINGS

Figure 1:
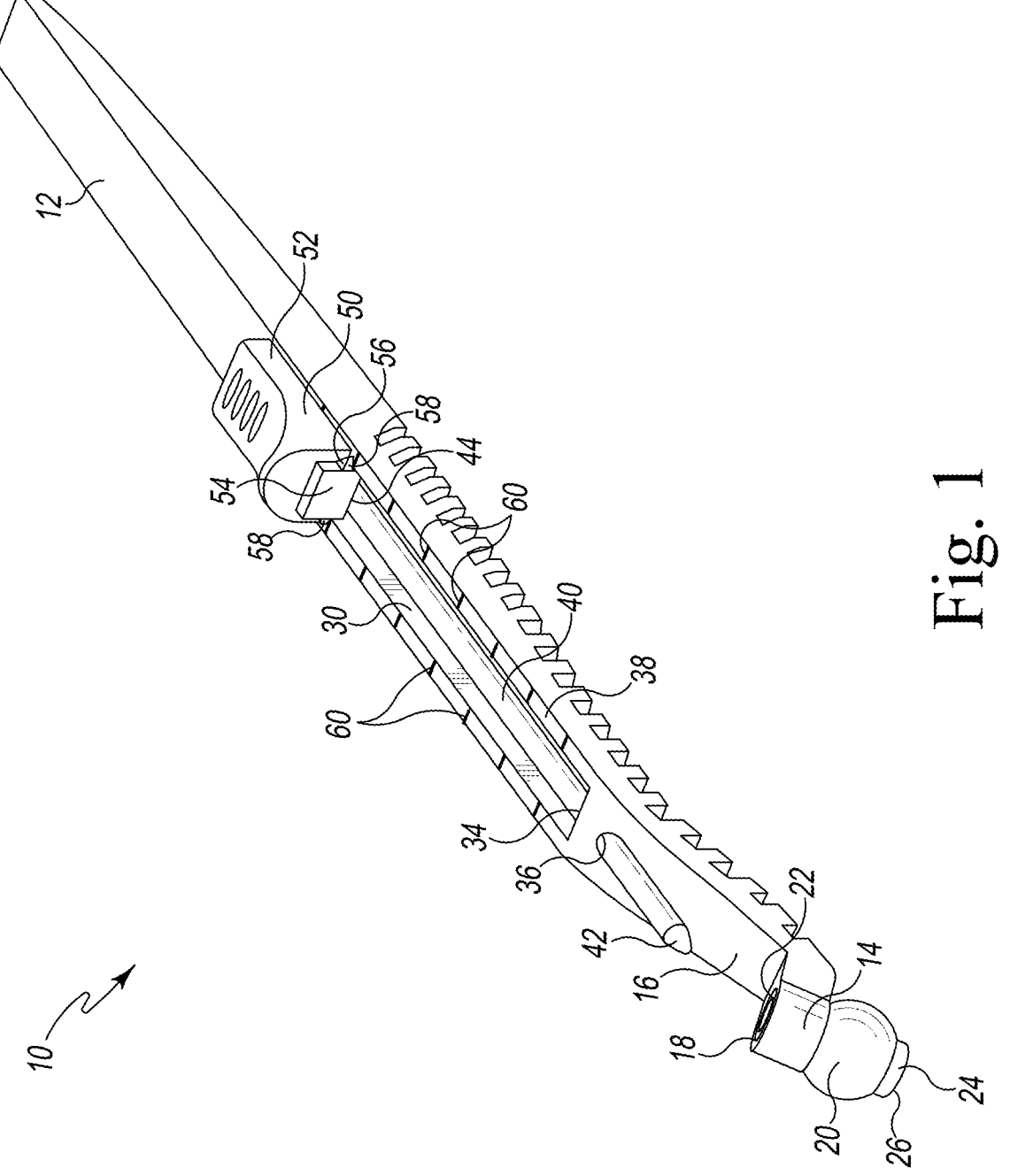
FIG. 1 is a perspective view of a combination drill guide and depth gauge surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-4, there is shown a combination drill guide and depth gauge surgical instrument 10 for use during a surgical procedure to implant an acetabular cup component into a surgically-prepared acetabulum of a patient's hip during an orthopaedic surgical procedure. As will be described in more detail below, the combination drill guide and depth gauge surgical instrument 10 may be embodied as a single-use surgical instrument that is disposed of after its use in a single orthopaedic surgical procedure (as opposed to being sterilized and reused in subsequent procedures). It should be appreciated that although the concepts of the present disclosure are herein described in regard to an instrument for use in an orthopaedic hip procedure, the concepts of the present disclosure may be utilized in the design of other types of orthopaedic instruments such as, but not limited to, instruments used in other types of orthopaedic surgical procedures including knee, shoulder, or ankle procedures.

The combination drill guide and depth gauge surgical instrument 10 includes an elongated body 12 having a drill guide 14 on its distal end 16. The drill guide 14 is cylindrically shaped and has a guide bore 18 extending through its entire length. As will be discussed below in more detail, the drill guide 14 is used to guide a bone drill during a drilling procedure to implant bone screws in the patient's acetabulum.

As will also be discussed below in more detail, in the illustrative embodiment described herein, the elongated body 12 is polymeric. In such an embodiment, the combination drill guide and depth gauge surgical instrument 10 may also include a metallic bushing 20. The metallic bushing 20 is overmolded, threaded, press-fit, or otherwise secured to the drill guide 14 such that the bushing 20 lines the guide bore 18 of the drill guide 14. Specifically, the metallic bushing 20 has a bore 22 that extends through its entire length. As such, the bushing 20 provides a metallic guide surface to receive the bone drill thereby preventing the drill from engaging the polymeric surfaces of the combination drill guide and depth gauge surgical instrument 10. It should be appreciated that depending on the type of materials utilized in the design of the combination drill guide and depth gauge surgical instrument 10 and the bone drill, the metallic bushing 20 may not be used.

As can be seen in FIG. 1, the metallic bushing 20 has an annular flange 24 defined in its distal end 26. As will be discussed below in greater detail, the annular flange 24 facilitates positioning of the drill guide 14 in the screw holes of the acetabular cup component being installed in the patient's hip.

As can be seen in FIGS. 1-4, the elongated body 12 has an elongated channel 30 formed therein. The channel 30 is arranged parallel to the longitudinal axis of the elongated body 12. The proximal end 32 of the channel 30 defines a blind end (see FIG. 2), whereas distal end 34 of the channel 30 is an open end. In particular, as can be seen in FIG. 1, an end wall defining the distal end 34 of the channel 30 has an opening 36 defined therein.

As can be seen in FIGS. 1-4, a depth probe 40 is positioned in the channel 30 of the elongated body 12. The depth probe 40 is embodied as an elongated, flexible probe having a distal tip 42 that extends out of the open distal end of the channel 30. In particular, the distal tip 42 of the depth probe 40 extends through the opening 36 defined at the distal end 34 of the channel 30. The proximal end 44 of the depth probe 40 is secured to a thumb actuator 50. In the illustrative embodiment of FIGS. 1-4, the thumb actuator 50 is embodied as a slider button 52 that is captured in the channel 30 so as to translate back and forth within it. As can be seen in FIG. 1, the proximal end 44 of the depth probe 40 is secured to the distal end 54 of the slider button 52.

Movement of the slider button 52 back and forth along the channel 30 causes corresponding movement of the depth probe 40. Specifically, movement of the slider button 52 in the direction toward the open distal end 34 of the elongated channel 30 causes the depth probe's distal tip 42 to be extended away from the open distal end 34 of the elongated channel 30. Oppositely, movement of the slider button 52 in a direction away the open distal end 34 of the elongated channel 30 causes the depth probe's distal tip 42 to be retracted back toward the open distal end 34 of the elongated channel 30.

Figure 2:
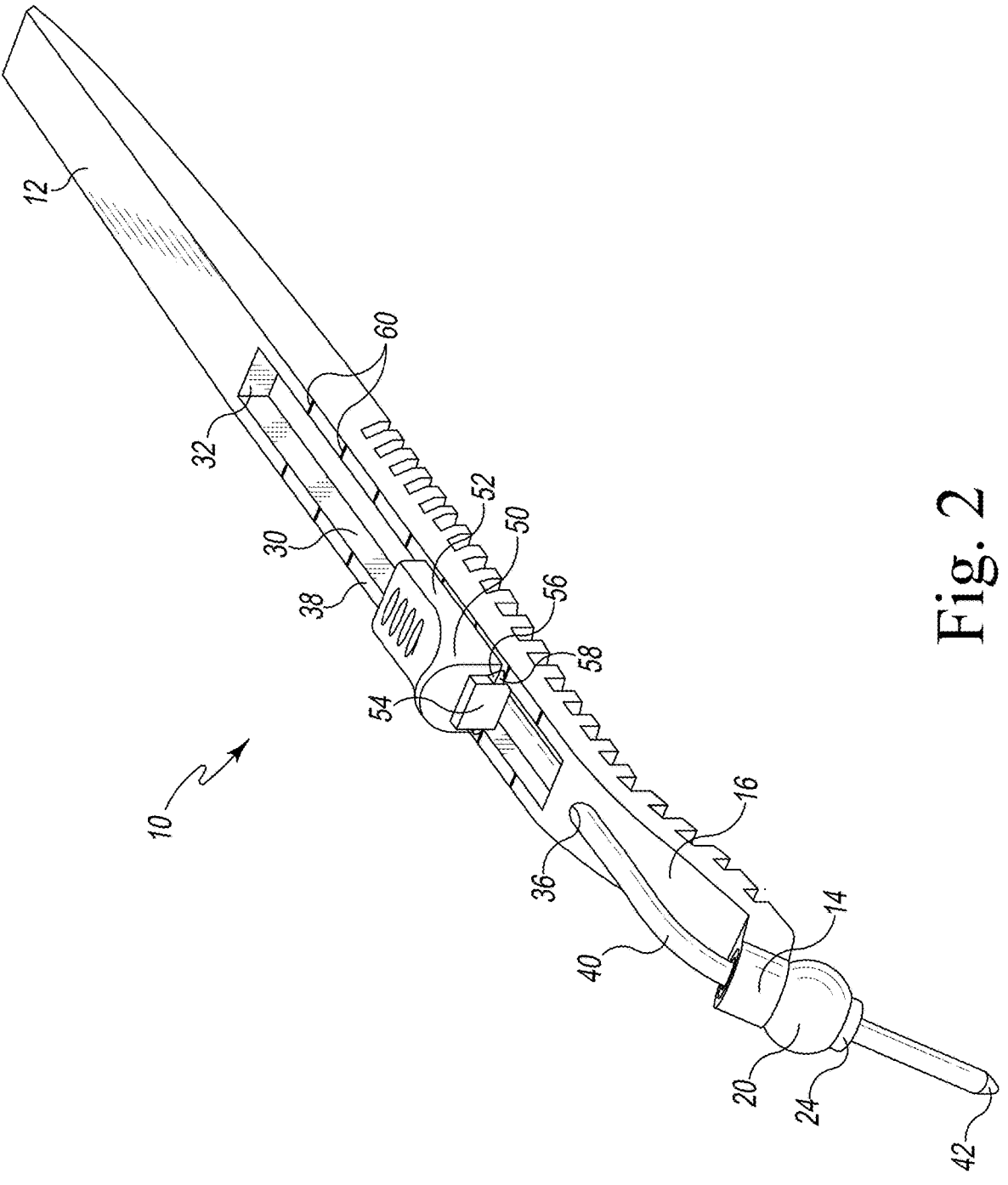
FIG. 2 is a view similar to FIG. 1, but showing the depth probe of the combination drill guide and depth gauge surgical instrument extending through the drill guide.
Figures 3, 4:
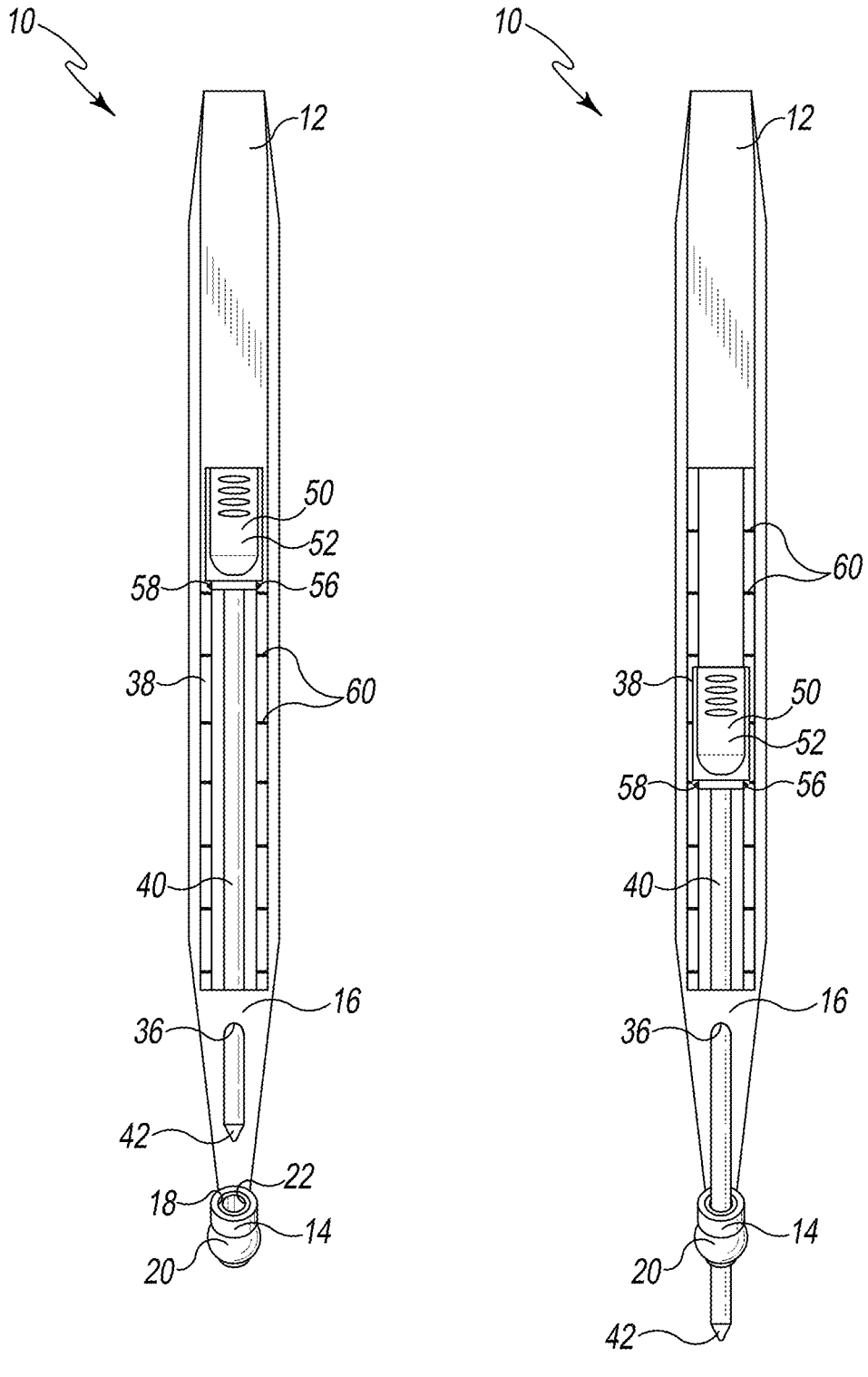
FIG. 3 is a plan view of the combination drill guide and depth gauge surgical instrument of FIG. 1.
FIG. 4 is a view similar to FIG. 3, but showing the depth probe of the combination drill guide and depth gauge surgical instrument extending through the drill guide.

Such movement allows the depth probe 40 to be used to determine the depth of holes drilled in the patient's hip after use of the drill guide 14. In particular, as shown in FIGS. 2 and 4, the distal tip 42 of the depth probe 40 is advanced into and through the guide bore 18 of the drill guide 14 as it is further extended out of the open distal end 34 of the elongated channel 30 by use of the slider button 52. As will be discussed below in more detail, the depth probe 40 may be advanced in such a manner until its distal tip 42 reaches the bottom of the hole previously drilled in the bone tissue by use of the drill guide 14 at which point the surgeon may then determine the depth of the drilled hole. To do so, the upper surface 38 of the elongated body 12 has a plurality of depth marks 60 disposed thereon. In the illustrative embodiment described herein, the depth marks 60 are molded into the elongated body 12; although they could also be disposed on the elongated body 12 in other manners such as by etching, surface printing, or formed in the elongated body 12 as part of an additive manufacturing process (e.g., 3D printing).

Each of the depth marks 60 is positioned on the elongated body 12 at a location that corresponds to a different, predetermined depth of the depth probe's distal tip 42. As can be seen in FIG. 1, the slider button 52 has disposed thereon a depth indicator 56 in the form of a pair of outwardly extending pointed tabs 58. As the slider button 52 is moved along the elongated channel 30, the pointed tabs 58 selectively align with a pair of the depth marks 60 one of which is located on each side of the channel 30. Each pair of depth marks 60 corresponds to a different depth of the drilled hole with the depth marks 60 located nearest the drill guide 14 corresponding to the deepest drilled holes. In other words, the depth marks 60 represent progressively deeper drilled holes as the slider button 52 approaches the drill guide 14.

As alluded to above, in the illustrative embodiment described herein, the combination drill guide and depth gauge surgical instrument 10 may be embodied as a single-use surgical instrument that is disposed of after its use in a single orthopaedic surgical procedure. As used herein, the term "disposed of"—as used in regard to disposition of the instrument after its use in an orthopaedic procedure for a particular patient—is that the instrument is discarded or otherwise never used again in regard to subsequent patients. As such, a single-use instrument that is disposed of after its use in one procedure is not sterilized and reused in subsequent procedures. In this regard, most of the components of the combination drill guide and depth gauge surgical instrument 10 are made of commercially-available and relatively inexpensive polymers. For example, the elongated body 12, the depth probe 40, and the slider button 52 may be fabricated with a polycarbonate.

Figure 5:
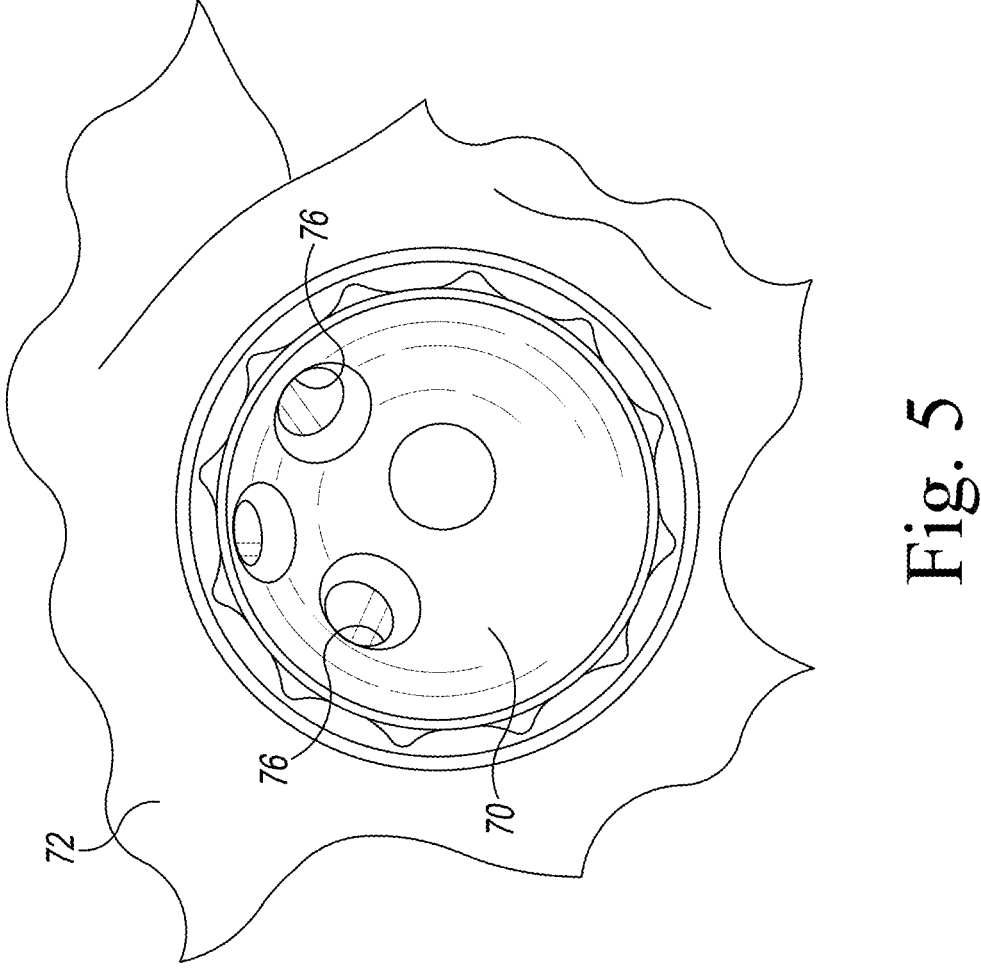
FIG. 5 is a perspective view showing an acetabular cup component positioned in a surgically-prepared acetabulum of a patient.

In use, as shown in FIGS. 5-8, the combination drill guide and depth gauge surgical instrument 10 may be utilized by a surgeon to implant an acetabular cup component 70 into the surgically-prepared acetabulum 72 of a patient. As shown in FIG. 5, the surgeon initially impacts or otherwise installs the acetabular cup component 70 into a hemispherically-shaped bone cavity reamed or otherwise surgically-formed in the patient's acetabulum 72.

Figure 6:
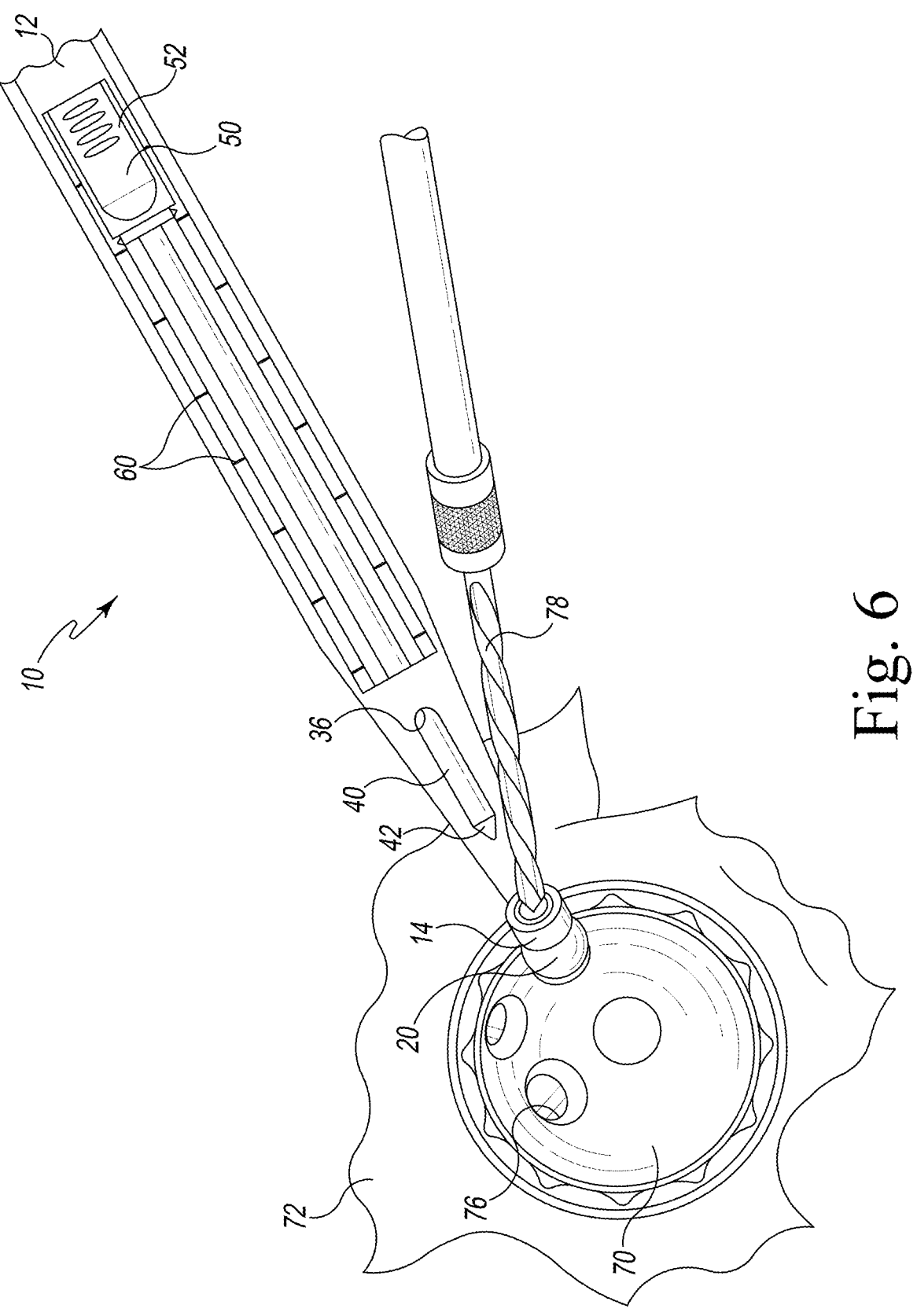
FIG. 6 is a perspective view showing underlying bone tissue of the patient's acetabulum being drilled by use of the combination drill guide and depth gauge surgical instrument of FIG. 1.

Thereafter, as shown in FIG. 6, the surgeon positions the drill guide 14 of the combination drill guide and depth gauge surgical instrument 10 in a desired position in the surgical site. In the illustrative embodiment described herein, the surgeon positions the annular flange 24 defined in the distal end 26 of the bushing into one of the screw holes 76 formed in the acetabular cup component 70. The surgeon then advances a bone drill 78 through the bore 22 of the metallic bushing 20 lining the guide bore 18 of the drill guide 14 and into the underlying bone tissue of the patient's acetabulum 72. The bone drill 78 is then removed from the drill guide 14.

Figure 7:
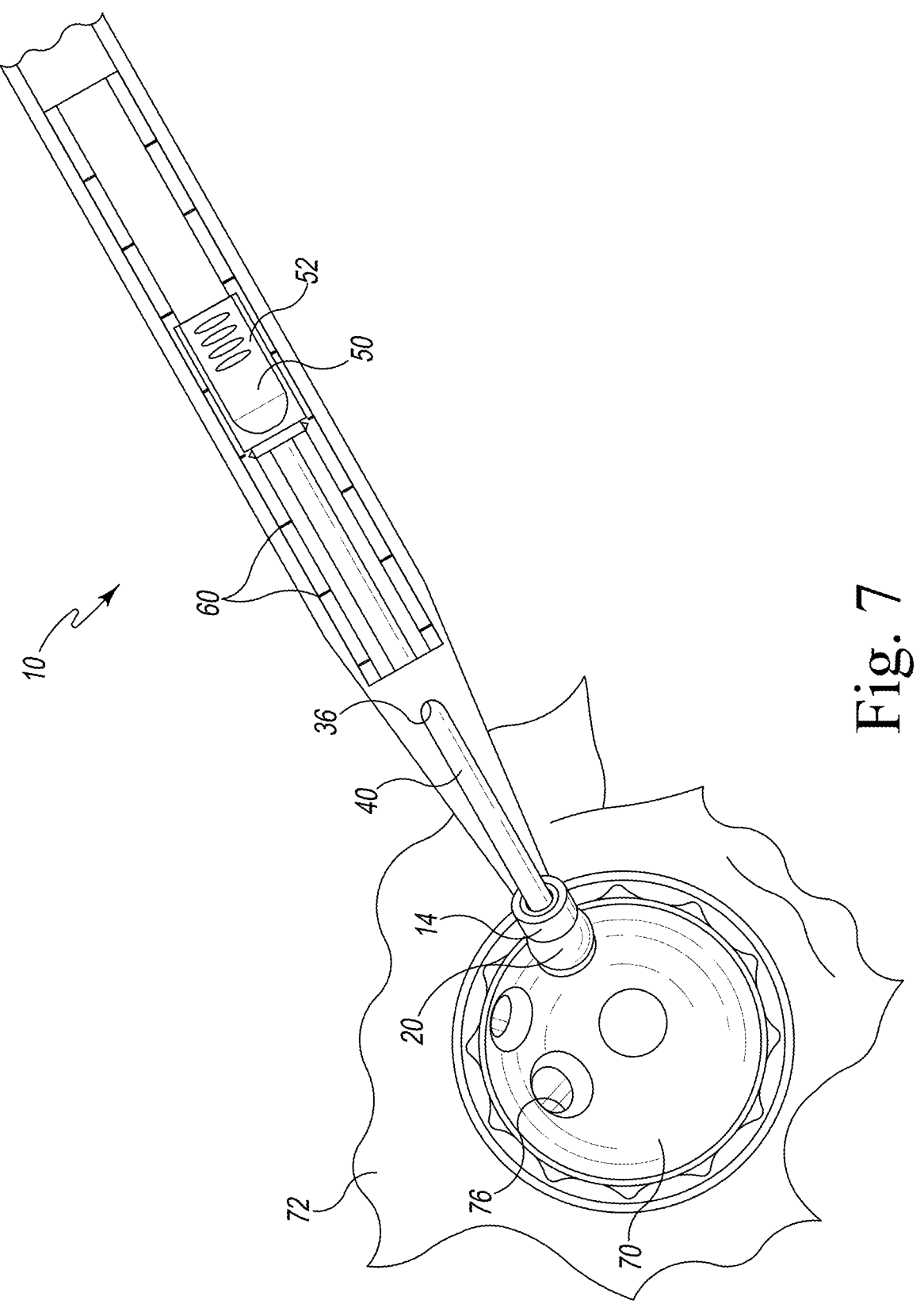
FIG. 7 is a perspective view showing the depth of the drilled hole being determined by use of the combination drill guide and depth gauge surgical instrument of FIG. 1.

As shown in FIG. 7, the surgeon then slides the slider button 52 in the direction toward the drill guide 14 such that the distal tip 42 of the depth probe 40 is advanced into and through the bore 22 of the metallic bushing 20 lining the guide bore 18 of the drill guide 14 and into the drilled hole in the underlying bone tissue of the patient's acetabulum 72. The surgeon continues to advance the slider button 52 until the depth probe's distal tip 42 bottoms out in the drilled hole. The surgeon then determines the depth of the drilled hole by observing the position of the depth indicator 56 (e.g., the pointed tabs 58) relative to the depth marks 60 on the elongated body 12. If the depth indicator 56 of the slider button 52 is aligned with the desired depth mark 60, the surgeon retracts the depth probe 40 by moving the slider button 52 in a direction away from the drill guide 14 and thereafter removes the combination drill guide and depth gauge surgical instrument 10 from the surgical site (i.e., removes it from contact with the acetabular cup component 70). If the depth indicator of the slider button 52 is not aligned with the desired depth mark 60, the surgeon retracts the depth probe 40 from the drill guide 14 by moving the slider button 52 in a direction away from the drill guide 14 and thereafter redrills the drilled hole to a deeper depth. The depth probe 40 may again be used to check the depth of the redrilled hole. The combination drill guide and depth gauge surgical instrument 10 may then be removed if the hole is now at the desired depth.

Figure 8:
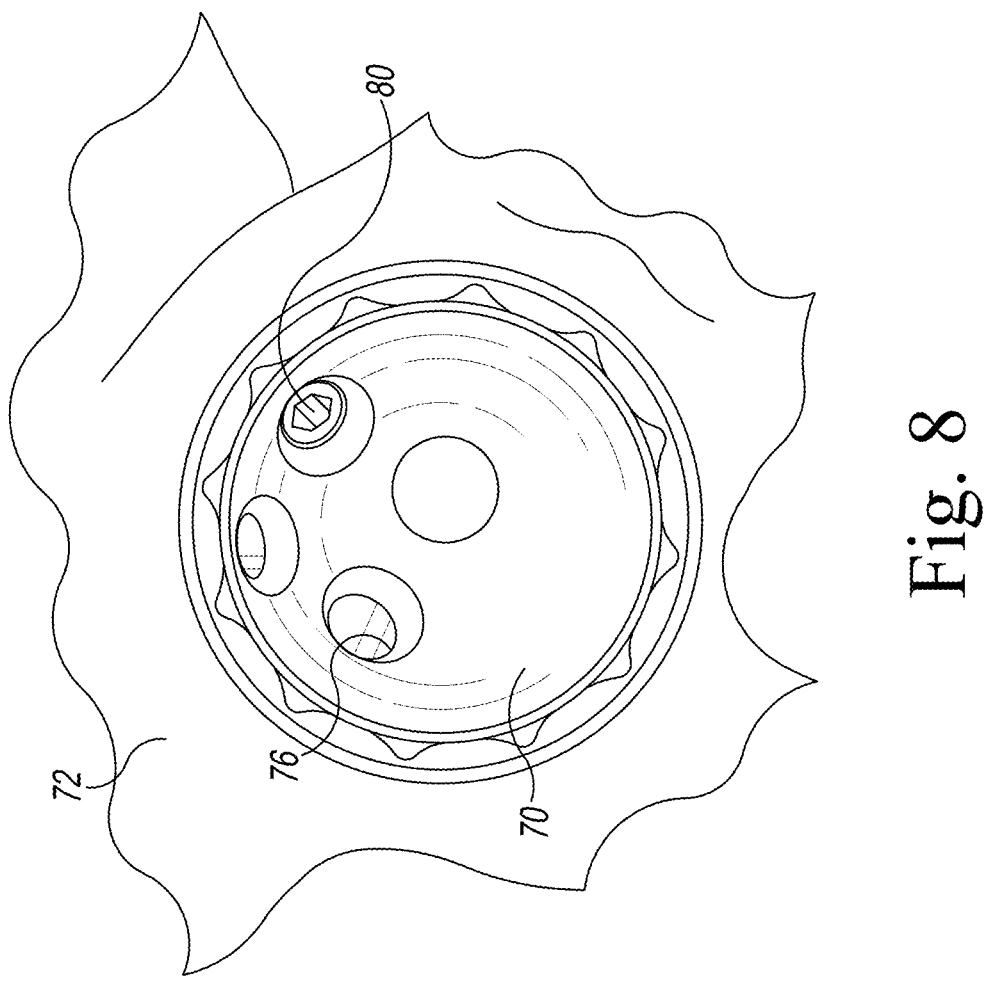
FIG. 8 is a perspective view showing a bone screw having been installed to secure the acetabular cup component to the surgically-prepared acetabulum of the patient.

As shown in FIG. 8, a bone screw 80 may then be inserted in the screw hole 76 formed in the acetabular cup component 70 and thereafter driven into the drilled hole so as to screw the acetabular cup component 70 the underlying bone tissue of the patient's acetabulum 72. The process may be repeated if the surgeon desires to install bone screws 80 in any of the remaining screw holes 76 formed in the acetabular cup component 70.

In the case of when the combination drill guide and depth gauge surgical instrument 10 is embodied as a single-use instrument, the instrument 10 is disposed of after the last of the bone screws 80 has been installed.

Figure 9:
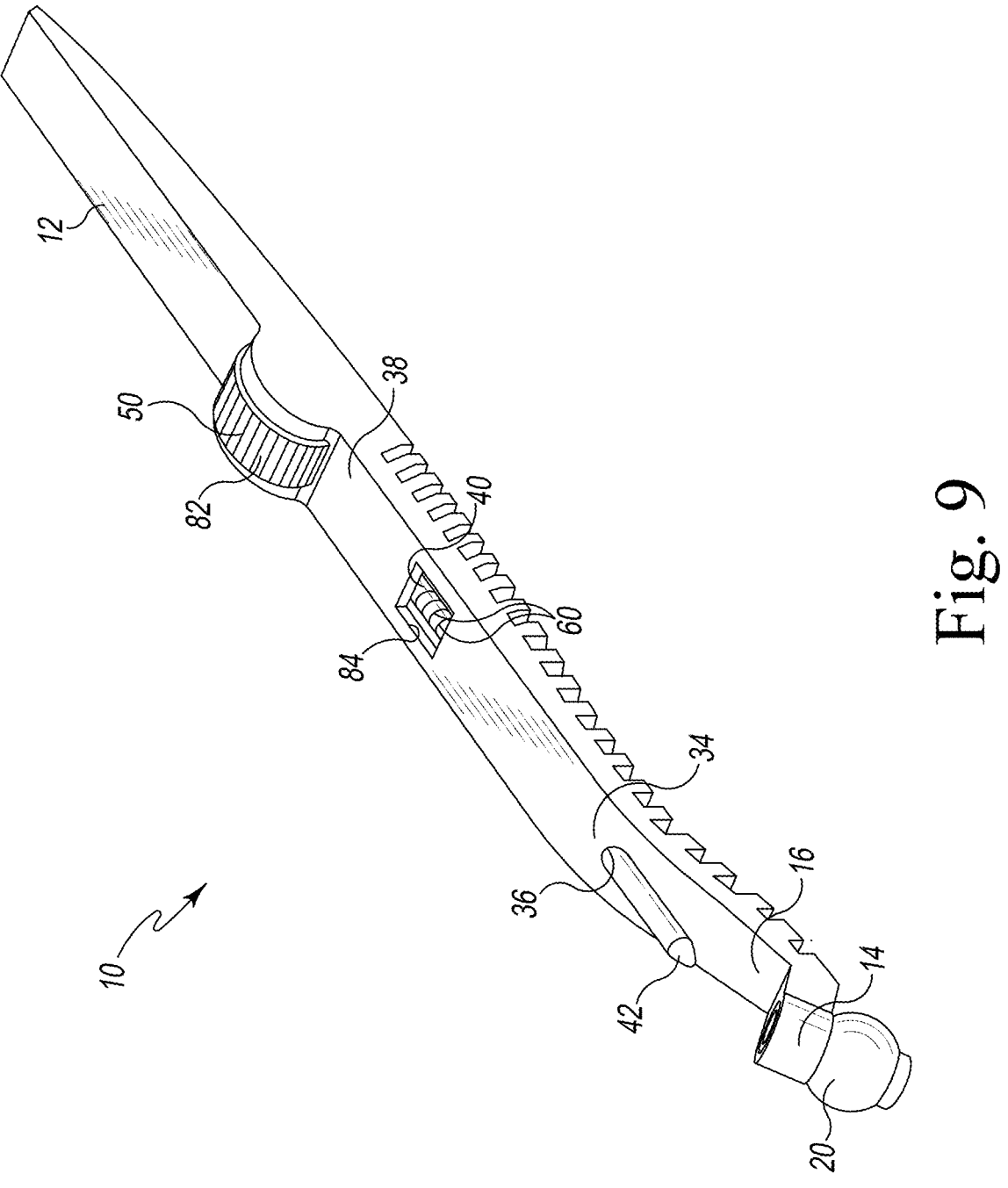
FIG. 9 is a view similar to FIG. 1, but showing another embodiment of the combination drill guide and depth gauge surgical instrument.

As shown in FIG. 9, other mechanisms for extending and retracting the depth probe 40 are contemplated for use in the design of the combination drill guide and depth gauge surgical instrument 10. For example, in lieu of the slider button 52, the thumb actuator 50 may be embodied as a knob 82 which frictionally engages or is otherwise operatively coupled to the depth probe 40. In such an embodiment, the knob 82 is rotatable relative to the elongated body 12 such that rotational movement of the knob 82 in the direction toward the open distal end 34 of the elongated channel 30 causes the depth probe's distal tip 42 to be extended away from the open distal end 34 of the elongated channel 30. Oppositely, rotational movement of the slider button 52 in a direction away the open distal end 34 of the elongated channel 30 causes the depth probe's distal tip 42 to be retracted back toward the open distal end 34 of the elongated channel 30. Such movement allows the depth probe 40 to be used to determine the depth of the holes drilled in the patient's hip after use of the drill guide 14 in a similar manner to as described above in regard to FIGS. 1-8.

In the illustrative embodiment of FIG. 9, the depth marks 60 are disposed on the depth probe 40 as opposed to the elongated body 12. In such case, the depth marks 60 are individually viewable through a viewing window 84 formed in the elongated body 12 and are therefore usable by the surgeon to determine the depth of the holes drilled in the underlying bone tissue of the patient's acetabulum 72 in a similar manner to as discussed above in regard to FIGS. 5-8.

Figure 10:
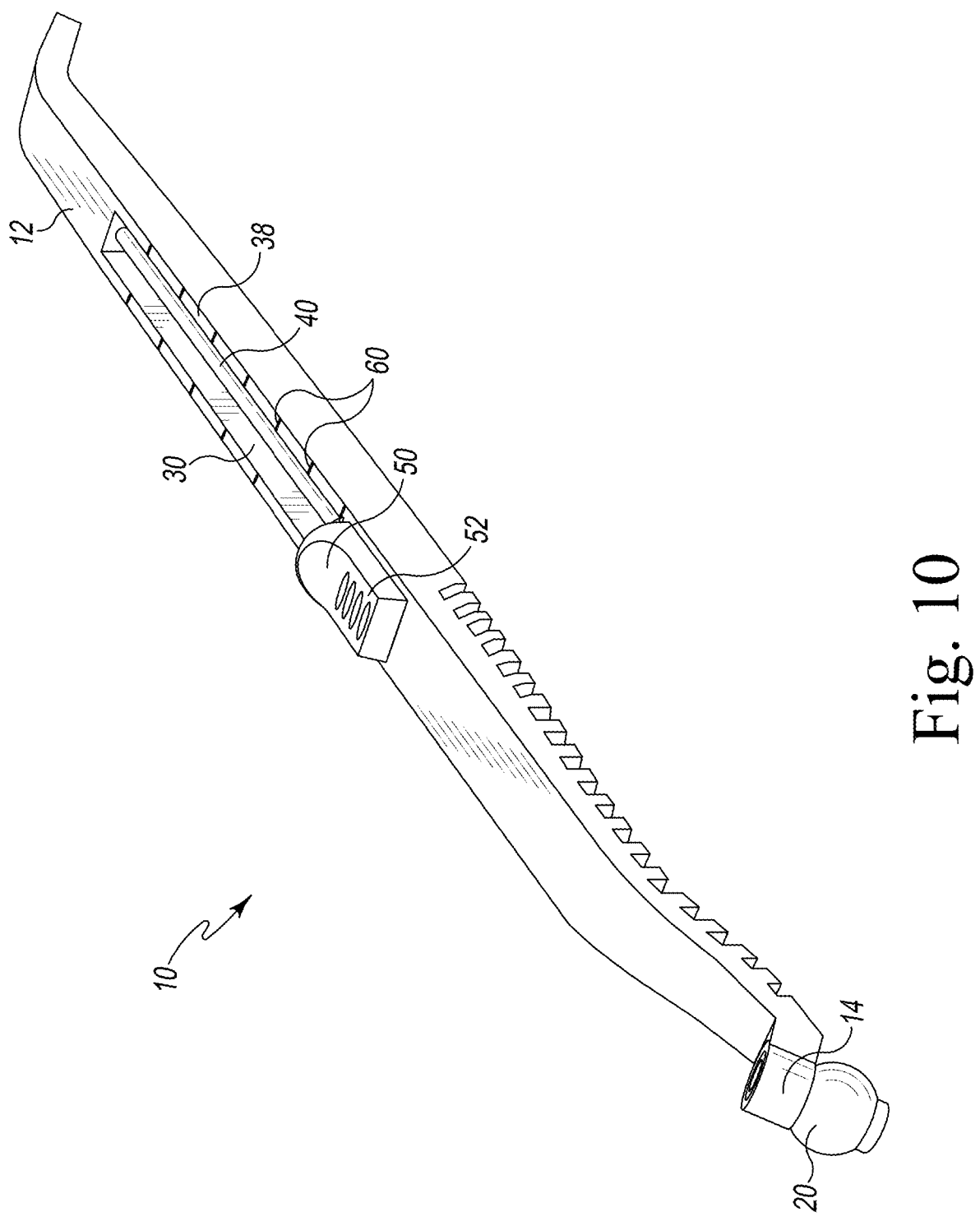
FIGS. 10 and 11 are perspective views showing yet another embodiment of the combination drill guide and depth gauge surgical instrument.
Figure 11:
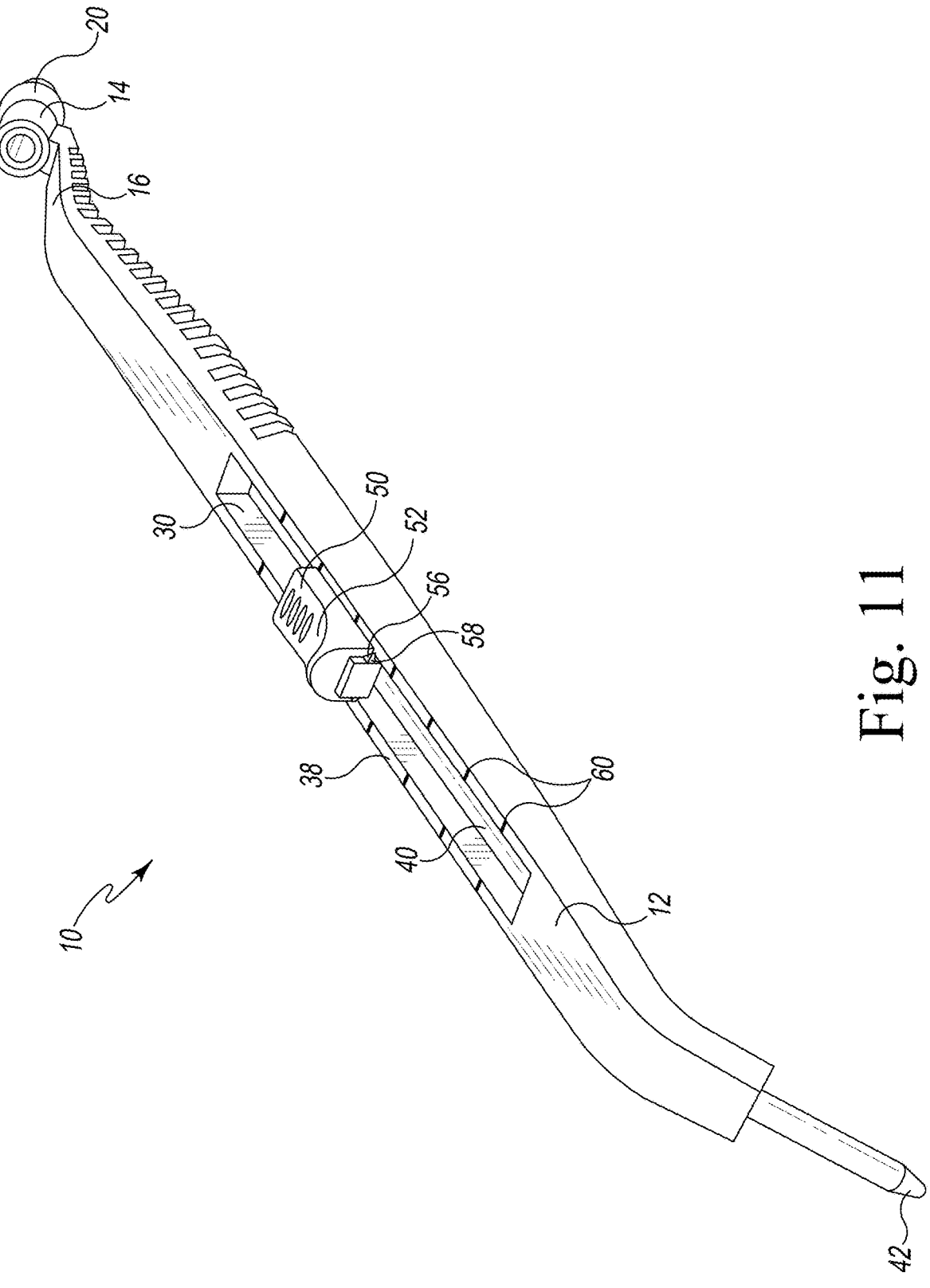

A further embodiment of the combination drill guide and depth gauge surgical instrument 10 is shown in FIGS. 10 and 11. In such an embodiment, the depth probe 40 is advanced out of the opposite end of the elongated body 12 from the drill guide 14. As such, movement of the thumb actuator 50 (e.g., the slider button 52) in a direction opposite the drill guide 14 causes extension of the depth probe 40. In the embodiment of the combination drill guide and depth gauge surgical instrument 10 shown in FIGS. 10 and 11, the surgeon flips the instrument 10 end-for-end to switch between use of the drill guide 14 and the depth probe 40.

Figure 12:
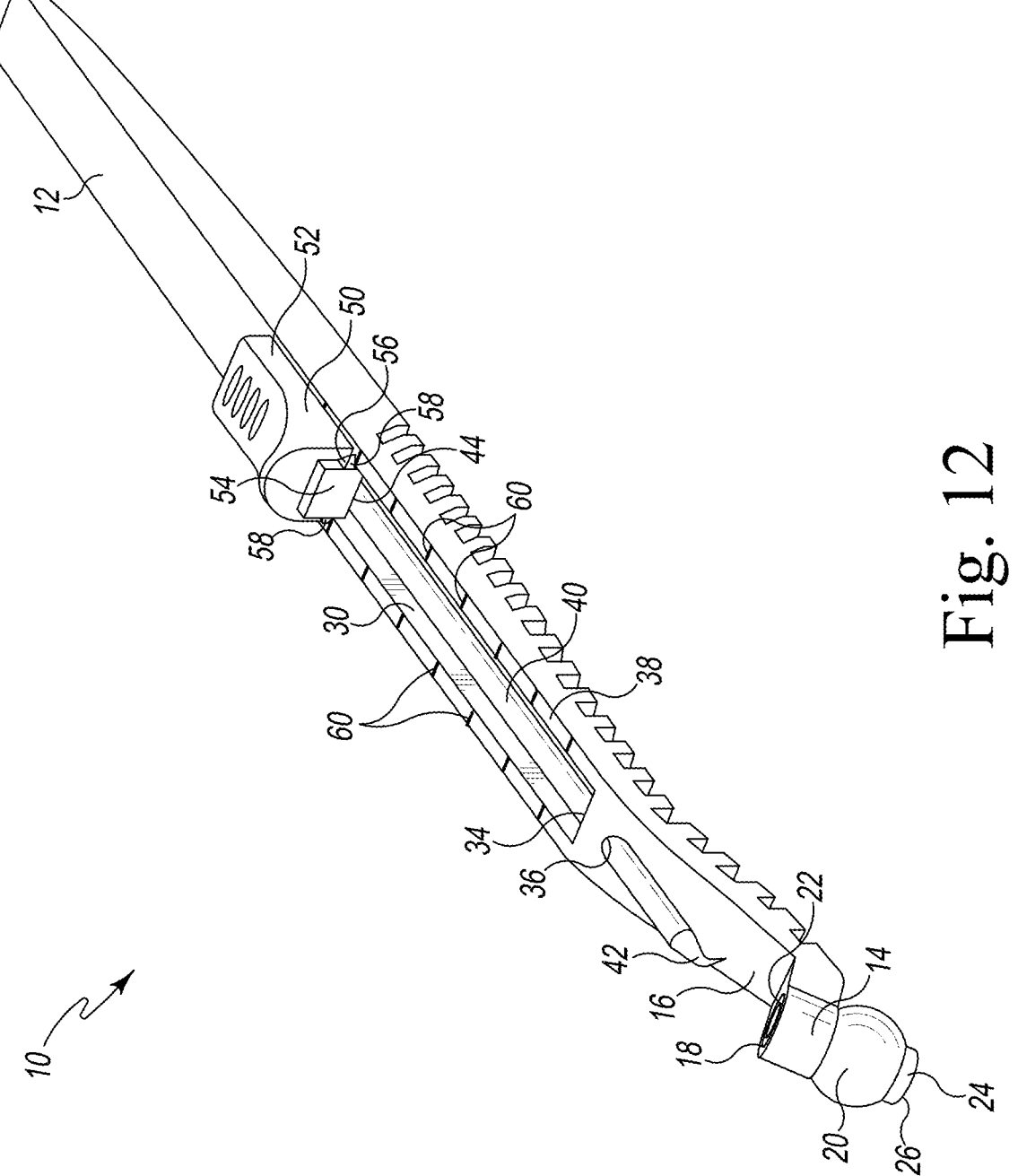
FIG. 12 is a view similar to FIG. 1, but showing another embodiment of the combination drill guide and depth gauge surgical instrument.

Yet another embodiment of the combination drill guide and depth gauge surgical instrument 10 is shown in FIG. 12. In such an embodiment, the distal tip 42 of the depth probe 40 has a relatively small bend formed in it such that the tip forms a hook-like structure. Such a hook-shaped distal tip 42 is useful in procedures in which the surgeon opts to drill completely through the bone tissue of the patient's acetabulum 72. In such a case, the hook-shaped distal tip 42 may be used to hook the backside of the bone to make the depth measurement/determination. It should be appreciated that the hook-shaped distal tip 42 is sized such that the tip 42 is able to readily pass through the drill guide 14. It should also be appreciated that the hook-shaped distal tip 42 may also be used in procedures in which the surgeon opts not to drill completely through the bone tissue of the patient's acetabulum 72 since it can effectively be used to determine when the depth probe 40 bottoms out in the drilled hole in the same manner as a probe 40 embodied with a conically-shaped distal tip 42.

It should be appreciated that the various embodiments described herein may be combined to fit the needs of a given design of the combination drill guide and depth gauge surgical instrument 10. For example, the design of FIGS. 10 and 11 in which the drill guide 14 and the depth probe 40 are positioned on opposite ends of the elongated body 12 may be used in conjunction with the knob 82 in lieu of the slider button 52. Moreover, the hook-shaped distal tip 42 of the design of FIG. 12 may be used in conjunction with any of the embodiments of the combination drill guide and depth gauge surgical instrument 10 of FIGS. 1-11.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:
1. A surgical instrument comprising:
an elongated body formed from a polymeric material, the elongated body having (i) a drill guide secured to an end thereof, the drill guide having a guide bore extend- ing therethrough and a metallic drill bushing positioned in the guide bore, and (ii) an elongated channel extending parallel to a longitudinal axis of the elongated body, the elongated channel including a distal end having an opening; and a depth probe positioned in the elongated channel; and a thumb actuator operable to move the depth probe from a first position in which the depth probe is retracted into the elongated channel relative to the opening of the distal end of the elongated channel and a second position in which the depth probe extends from the opening of the distal end of the elongated channel and through the guide bore of the drill guide.

2. The surgical instrument of claim 1, wherein:

the thumb actuator comprises a slider button secured to the depth probe and configured to slide along an upper surface of the elongated body, wherein movement of the slider button in a direction away from the opening of the distal end of the elongated channel moves the depth probe toward the first position and movement of the slider button in a direction toward the opening of the distal end of the elongated channel moves the depth probe toward the second position.

3. The surgical instrument of claim 2, wherein the upper surface of the elongated body has a plurality of depth marks disposed thereon, wherein each of the plurality depth marks is positioned at a location on the upper surface of the elongated body corresponding to a depth of a distal tip of the depth probe, and wherein the slider button has a depth indicator disposed thereon, the depth indicator being alignable with one of the plurality of depth marks based on the position of the slider button.

4. The surgical instrument of claim 1, wherein the thumb actuator comprises a knob operatively coupled to the depth probe and rotatable relative to the elongated body, wherein rotational movement of the knob in a direction away from the open end of the elongated channel moves the depth probe toward the first position and rotational movement of the knob in a direction toward the open end of the elongated channel moves the depth probe toward the second position.

5. The surgical instrument of claim 4, wherein the depth probe has a plurality of depth marks disposed thereon, wherein each of the plurality of depth marks is positioned at a location on the depth probe corresponding to a depth of the depth probe's distal tip.

6. The surgical instrument of claim 1, wherein the thumb actuator comprises a knob operatively coupled to the depth probe and rotatable relative to the elongated body, wherein rotational movement of the knob in a direction toward the open end of the elongated channel moves the depth probe toward the first position and rotational movement of the knob in a direction away from the open end of the elongated channel moves the depth probe toward the second position.

7. The surgical instrument of claim 6, wherein the depth probe has a plurality of depth marks disposed thereon, wherein each of the plurality of depth marks is positioned at a location on the depth probe corresponding to a depth of the depth probe's distal tip, and wherein an upper surface of the elongated body has a viewing window formed therein and one of the plurality of depth marks is viewable through the viewing window based on an amount and direction of rotational movement of the knob.

8. The surgical instrument of claim 1, wherein the elongated body is formed from a polymeric material, and the depth probe is formed from a flexible polymeric material.

9. The surgical instrument of claim 1, wherein the depth probe includes a hook-shaped distal tip, wherein the hook-shaped distal tip is retracted into the elongated channel when the depth probe is in the first position and the hook-shaped distal tip extends through the guide bore of the drill guide when the depth probe is in the second position.

10. A surgical instrument comprising:

a body having an elongated handle and a drill guide secured to an end of the elongated handle, wherein the elongated handle defines a longitudinal axis and includes an elongated channel extending parallel to the longitudinal axis and wherein the drill guide includes a guide bore extending therethrough and defining an axis that intersects the longitudinal axis;

a depth probe positioned in the elongated channel, the depth probe having a hook-shaped distal tip extending out of an open end of the elongated channel, and an actuator movable relative to the elongated handle and operable to move the depth probe such that the depth probe's hooked-shaped distal tip is extended and retracted relative to the open end of the elongated channel.

11. The surgical instrument of claim 10, wherein the open end of the elongated channel is located on an end of the elongated handle opposite the end of the elongated handle to which the drill guide is secured.

12. The surgical instrument of claim 10, further comprising a metallic drill bushing positioned in the guide bore of the drill guide.

13. The surgical instrument of claim 12, wherein the metallic drill bushing includes an annular flange located on a distal end of the metallic drill bushing.

14. The surgical instrument of claim 12, wherein the elongated handle is formed from polymeric material.

15. The surgical instrument of claim 10, wherein the elongated handle is formed from a polymeric material, and the depth probe is formed from a flexible polymeric material.

16. A method of implanting an acetabular cup component into a surgically-prepared acetabulum of a patient's hip, comprising:

positioning a drill guide of a combination drill guide and depth gauge surgical instrument in a desired position within the surgically-prepared acetabulum of the patient's hip, advancing a bone drill through drill guide and drilling a hole into bone tissue of the patient's hip, removing the bone drill from the drill guide, and advancing a depth probe of the combination drill guide and depth gauge surgical instrument through the drill guide and determining a depth of the drilled hole.

17. The method of claim 16, further comprising:

installing a bone screw in the drilled hole after determining the depth of the drilled hole.

18. The method of claim 17, wherein the combination drill guide and depth gauge surgical instrument comprises a single-use instrument, further comprising the step of:

disposing of the combination drill guide and depth gauge surgical instrument subsequent to installation of the bone screw.

* * * * *